United States Patent [19]
Horrobin et al.

[11] Patent Number: 5,866,703
[45] Date of Patent: Feb. 2, 1999

[54] TRIGLYCERIDES

[75] Inventors: David F. Horrobin, Guildford; Austin McMordie, Carlisle; Mehar Singh Manku, Carlisle; Philip Knowles, Carlisle, all of England

[73] Assignee: Scotia Holdings PLC, United Kingdom

[21] Appl. No.: 543,799

[22] Filed: Oct. 16, 1995

Related U.S. Application Data

[63] Continuation of Ser. No. 187,046, Jan. 27, 1994, abandoned.

[30] Foreign Application Priority Data

Jan. 27, 1993 [GB] United Kingdom .................. 9301582
Jan. 29, 1993 [GB] United Kingdom .................. 9301801

[51] Int. Cl.$^6$ .................................................... C07C 57/00
[52] U.S. Cl. ........................... 554/227; 554/223; 554/224; 514/547
[58] Field of Search ..................... 554/223, 224, 554/227; 514/547

[56] References Cited

U.S. PATENT DOCUMENTS 5,151,291  9/1992  Tokairin .................. 554/224

FOREIGN PATENT DOCUMENTS 0 520 624 A1  5/1992  European Pat. Off. .
WO 94/10125  5/1994  WIPO .

OTHER PUBLICATIONS

*J. High Resolut. Chromatogr.*, vol. 15, No. 4, 1992, pp. 219–226: Aitzetmuller: "Separation of Highly Unsaturated Triacylglycerlos by Reversed Phase HPLC with Short Wavelength UV Detection ".

JAOCS vol. 66, No. 9, 1989 pp. 1330–1333 Osterberg "Lipase catalyzed transesterification of unsaturated lipids in a Microemulsion".

JAOCS vol. 66, No. 7, 1989 pp. 966–969 Ratnayake "Triacylglycerols of evening primrose (Oenothera biennis) seed oil".

STN International Karlsruhe Fiel "CA", Chemical Abstracts AN=CA115(25):278299d. Osada Molecular species of enzymically–synthesized polyunsaturated fatty acid–rich triglycerides & Nippon Suisan Gakkaishi,m 57(1), 119–25, 1991.

*Primary Examiner*—Gary Geist
*Assistant Examiner*—Deborah D Carr
*Attorney, Agent, or Firm*—Nixon & Vanderhye

[57] ABSTRACT

Triglycerides with at least two different acids chosen from 6-desaturated essential fatty acids and oleic acid, useful in nutrition and in medicine.

9 Claims, No Drawings

TRIGLYCERIDES

This is a continuation of application Ser. No. 08/187,046, filed 27 Jan. 1994, now abandoned.

FIELD OF INVENTION

The invention relates to triglycerides.

BACKGROUND

The essential fatty acids (EFAs) consist of a series of twelve compounds illustrated in Table 1 below. Although linoleic acid the parent compound of the n-6 series of EFAs, and alpha-linolenic acid the parent compound of the n-3 series, are usually the main dietary EFAs, these substances as such have relatively minor roles in the body. In order to be fully useful to the body, the parent compounds must be metabolized by the sequence of reactions shown in Table 1. In quantitative terms, as judged by their levels in cell membranes and in other lipid fractions, dihomo-gamma-linolenic acid (DGLA) and arachidonic acid (AA) are the main EFA metabolites of the n-6 series, while eicosapentaenoic acid (EPA) and docosahexaenoic acid (DHA) are the main metabolites of the n-3 series. DGLA, AA, EPA and DHA are important constituents of most of the lipids in the body. As well as being important in themselves they can also give rise to a wide range of oxygenated derivatives, the eicosanoids, including the prostaglandins, leukotrienes and other compounds.

The elongation reactions shown in Table 1, in which 2 carbon atoms are added to the chain, tend to be rapid, whereas the desaturation reactions in which an extra double bond is introduced tend to be very slow. Thus for example gamma-linolenic acid (GLA) is rapidly converted to DGLA while stearidonic acid is readily converted to 20:4n-3 and so these pairs of compounds are equivalent in dietary terms. However, DGLA is only slowly converted to AA. The reactions are not normally reversible nor, in man, are n-3 and n-6 series acids inter-convertible.

The table is as follows:

TABLE 1

| n-6 | | n-3 |
|---|---|---|
| 18:2 delta-9,12 (linoleic acid) | | 18:3 delta-9,12,15 (alpha-linolenic acid) |
| | delta-6 desaturase | |
| 18:3 delta-6,9,12 (gamma-linolenic acid) | ↓ | 18:4 delta-6,9,12,15 (stearidonic acid) |
| | elongation | |
| 20:3 delta-8,11,14 (dihomo-gamma-linolenic acid) | ↓ | 20:4 delta-8,11,14,17 |
| | delta-5 desaturase | |
| 20:4 delta-5,8,11,14 (arachidonic acid) | ↓ | 20:5 delta-5,8,11,14,17 ('eicosapentaenoic acid') |
| | elongation | |
| 22:4 delta-7,10,13,16 (adrenic acid) | ↓ | 22:5 delta-7,10,13,16,19 |
| | delta-4 desaturase | |
| 22:5 delta-4,7,10,13,16 | ↓ | 22:6 delta-4,7,10,13,16,19 ('docosahexaenoic acid') |

The acids, which in nature are of the all-cis configuration, are systematically named as derivatives of the corresponding octadecanoic, eicosanoic or docosanoic acids, e.g. delta-9, 12-octadecadienoic acid or delta-4,7,10,13,16, 19-docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used.

Disease States

It is becoming apparent that in many different disease states there are abnormalities of EFA biochemistry leading to abnormal EFA levels in various lipid fractions and in various tissues. These diseases include diseases of the heart and circulation such as hypertension and coronary and peripheral vascular disease, diseases of inflammation and immunity such as atopic disorders, osteoarthritis, rheumatoid arthritis, ulcerative colitis, Crohn's disease and various disorders going under the general classifications of inflammatory or auto-immune, neurological disorders such as Alzheimer's disease, Parkinson's disease and multiple sclerosis, disorders of the kidney, disorders of the skin, disorders of the gastrointestinal tract, disorders of metabolism of calcium and other minerals, disorders of bone and connective tissue, disorders of the reproductive and endocrine systems, psychiatric disorders including schizophrenia, and disorders of aging.

It used to be thought sufficient, both in nutrition and in therapy of disease, to supply linoleic and alpha-linolenic acids and the body's own metabolism would invariably do the rest. It has now been evident for some time that this is not true. Different diseases have different abnormal patterns of EFAs and because of problems in metabolism these cannot be corrected simply by giving linoleic acid or alpha-linolenic acid. Many examples of this type of situation are given in papers and prior patents by the inventor. Relevant papers include Horrobin D.F. Rev. Contemporary Pharmacotherapy 1990: 1:1–41, Horrobin D.F. Progress Lipid Res 1992: 31: 163–194 and Horrobin D.F. and Manku M.S. pp. 21–53 in "Omega-6 Essential Fatty Acids" Ed. Horrobin, D.F. New York: Wiley-Liss, 1990

It is therefore desirable in some situations to give two or more of the EFAs simultaneously. For this purpose the EFAs may be divided into the following groups:

i) GLA and DGLA ii) AA and its metabolites adrenic acid and the 22:5n-6 acid iii) Stearidonic acid (SA) and the 20:4n-3 acid iv) EPA and its metabolites the 22:5n-3 acid and DHA.

Moreover, the EFAs are exceptionally susceptible to oxidation and so it may be appropriate to co-administer the EFAs with oleic acid (OA) which has potent properties as an antioxidant.

While the EFAs can be supplied in various forms and in various mixtures, it is in principle convenient in both nutrition and in medical treatment to be able to supply the fatty acids as predetermined, particular molecules. This is particularly true with respect to pharmaceuticals, where regulations and directives covering combination products are becoming steadily more restrictive. For example, in order to win government approval for a combination drug product containing compounds A, B and C, it is now no longer adequate to mix the three compounds together in formulation X, and then to compare X with placebo, P. Many governments now require proof of the value of each individual chemical entity, whether or not the whole point of a proposal is a synergistic action of different entities or a newly discovered simultaneous lack of more than one entity. Therefore at the very least clinical studies have to be set up comparing P with X, with A alone, with B alone and with C alone. Some governments might also require comparisons with A+B, A+C and B+C. Thus at least five and possibly eight groups would be required for testing with an enormous escalation of cost. In order to avoid this situation, it would be appropriate instead of having a mixture of A, B and C, to have a single molecule in which A, B and C are found together in the same chemical compound, Y, allowing direct and simple testing of Y against P with only two groups required. For this purpose triglycerides, which can contain three fatty acids, are proposed.

Triglyceride Structures

In triglycerides the above different groups of EFAs and oleic acid may be present in the same molecule, either randomly distributed among the 1, 2 and 3 positions or with a particular EFA being found specifically in one of the positions on the molecule. With each triglyceride one or two positions will be occupied by one fatty acid while the other one or two positions will be occupied by one or two other fatty acids.

In glycerol $$^1CH_2OH$$
$$|$$
$$^2CHOH$$
$$|$$
$$^3CH_2OH$$

the 1 and 3 positions. while formally identical, in derivatives may not be functionally so. A triglyceride with three different fatty acids X, Y and Z is chiral at $C_2$ and four structures can notionally be drawn:

TABLE 2

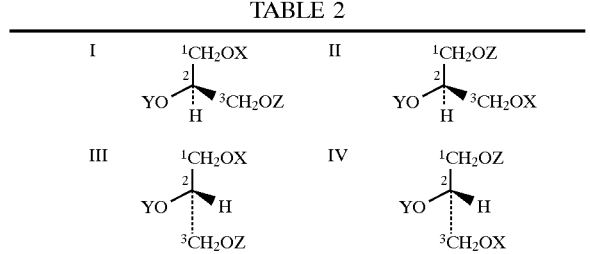

In solution, II is identical to III, which is the optical isomer of I, as can be seen by considering rotation of the molecule about the bond to YO—to bring —$CH_2OX$ to the top, and the same is so of I and IV. However in biological systems where a receptor favours bonding groups in a given relative position, it may be preferable or even necessary to have one isomer or the other.

In Preparing Triglycerides

The course of esterification may in principle be directed to favour a desired isomer, but if it is not, then the position of individual acid residues in the triglycerides produced from starting mixtures of two acids is one of the several possibilities:

TABLE 3a

AAA AAB*
ABA ABB*
BAB
BBB and for three different acids:

TABLE 3b

AAA AAB* AAC*
ABA ABB* ABC*
ACA ACB* ACC*
BAB BAC*
BBB BBC*
BCB BCC*
CAC
CBC
CCC with either isomer equally likely to be formed where $C_2$ is chiral, at least in chemical as opposed to enzymatic synthesis. What the two or three acids are, of course, depends on the choices made from the possible acids. What the preparations of the isomers are is calculable, for undirected synthesis.

The Invention

In the light of the above the invention provides, as groups of isomers or singly, triglycerides containing:

a) two residues of an acid selected from oleic acid and the following groups of the acids of table 1:

Group 1 GLA and DGLA

Group 2 AA, adrenic acid, and the 22:5 n-6 acid

Group 3 stearidonic acid and the 20:4 n-3 acid

Group 4 EPA, the 22:5 n-3 acid, and DHA and one residue of an acid selected differently therefrom; or b) one residue of an acid selected from oleic acid and the acids of groups i) to iv) above, one residue of an acid selected differently therefrom, and one residue of an acid selected differently again therefrom; with the proviso that where an acid has been selected from one group a subsequent selection is not from that same group.

The groups of isomers so defined comprise mixtures of positional and/or optical isomers, which may be in the proportions arising from directed or undirected synthesis, or in proportions arising from treatment of as-synthesised mixtures to enhance the proportion of particular isomers or groups of isomers. Further, according to the method of synthesis and degree of enhancement if any, varying amounts of triglycerides other than those defined may also be present.

The selection of desired groups of isomers may also be tabulated as below, with arbitrary reference numbers for the triglycerides (TGs), or rather possible groups of triglyceride isomers represented. For example TG1 is the possible di-Group1-mono-Group4glycerides eg. the di-(gammalinolenoyl)-mono-(eicosapentanoyl) glycerides. The table is:

TABLE 4

| TG | Oleic | Group 1 | Group 2 | Group 3 | Group 4 |
|----|-------|---------|---------|---------|---------|
| 1  | —     | 2       | —       | —       | 1       |
| 2  | —     | 2       | 1       | —       | —       |
| 3  | 1     | 2       | —       | —       | —       |
| 4  | —     | 2       | —       | 1       | —       |
| 5  | —     | 1       | —       | —       | 2       |
| 6  | —     | 1       | 2       | —       | —       |
| 7  | 2     | 1       | —       | —       | —       |
| 8  | —     | 1       | —       | 2       | —       |
| 9  | —     | 1       | 1       | —       | 1       |
| 10 | 1     | 1       | —       | —       | 1       |
| 11 | —     | 1       | —       | 1       | 1       |
| 12 | 1     | 1       | 1       | —       | —       |
| 13 | —     | 1       | 1       | 1       | —       |
| 14 | 1     | 1       | —       | 1       | —       |
| 15 | —     | —       | 1       | —       | 2       |
| 16 | 1     | —       | —       | —       | 2       |
| 17 | —     | —       | —       | 1       | 2       |
| 18 | —     | —       | 2       | —       | 1       |
| 19 | 2     | —       | —       | —       | 1       |
| 20 | —     | —       | —       | 2       | 1       |
| 21 | 1     | —       | 1       | —       | 1       |
| 22 | —     | —       | 1       | 1       | 1       |
| 23 | 1     | —       | —       | 1       | 1       |
| 24 | 1     | —       | 2       | —       | —       |
| 25 | —     | —       | 2       | 1       | —       |
| 26 | 2     | —       | 1       | —       | —       |
| 27 | —     | —       | 1       | 2       | —       |
| 28 | 1     | —       | 1       | 1       | —       |
| 29 | 2     | —       | —       | 1       | —       |
| 30 | 1     | —       | —       | 2       | —       |

As well as in structural terms as above, the invention may be considered in terms of starting mixtures of acids, selected from oleic acid and the acids of Groups 1–4 above, namely in molar terms (66% stands for two thirds, 33% for one third):

i) 66% of an acid selected from oleic acid and the acids of Groups 1, 2, 3 and 4, and 33% of a different acid selected therefrom; or ii) 33% of an acid selected from oleic acid and the acids of Groups 1, 2, 3 and 4; 33% of a different acid selected therefrom; and 33% of another different acid selected therefrom.

Preferred starting mixtures, with arbitrary reference numbers for the triglycerides, or rather possible groups of triglyceride isomers (TGs), that they formally represent, are derived from Table 4, specifying numbers of residues, by reading 66 mole % (two thirds) for '2' and 33 mole % (one third) for '1'.

As the desire is to give mixed triglycerides of two or three acids, species AAA and BBB of Tables 3a and 3b are for example unwanted components of the synthesized mixture, but the mixed species predominate and the as-synthesized mixtures are therefore valuable. Where the desire specifically is to give mixed triglycerides of three acids, such species do not predominate but are still present in a valuable proportion. In either case desired species can be separated or part separated from others by chromatographic or other methods known in themselves.

Individual triglycerides, either containing three different fatty acids, or two fatty acids in a 2:1 ratio, may thus be manufactured by chemical or enzymatic means by methods known in themselves to those skilled in the art. If the method of synthesis or manufacture does not provide an adequate concentration of the desired triglyceride, then that triglyceride may be concentrated and purified by appropriate techniques as outlined later.

As far as we are aware, all the groups of triglyceride isomers defined as above consist of new triglycerides which do not appear in nature and have not previously been described. They may broadly be prepared as follows:

a) The individual fatty acids are purified from natural animal, vegetable or microbial sources or are chemically synthesized, there being methods known in themselves to those skilled in the art.

b) The individual fatty acids are then esterified with glycerol by chemical or enzymatic methods, there being again methods known in themselves to those skilled in the art. For example, the fatty acids and glycerol may be allowed to react together in the presence of one of a number of appropriate enzymes, or of p-toluene sulphonic acid hydrate.

c) If required, the specific triglycerides are further purified by appropriate methods, again known to those skilled in the art, in particular high pressure liquid chromatography or other appropriate forms of chromatography; low temperature crystallisation; or the use of solvents which differentially select triglycerides of particular composition.

In the product, desirably a specified particular triglyceride or group of triglycerides forms more than 10%, preferably more than 30% very preferably more than 70% and ideally more than 90% of the triglycerides present in any triglyceride mixture used for the preparation of pharmaceutical compositions, foods, or skin care products. The triglycerides may be made up into appropriate pharmaceuticals or foods so as to provide a daily dose of 1 mg to 100 g per day, preferably 10 mg to 10 g and very preferably 500 mg to 4 g. Alternatively in foods or skin care products the triglycerides may be incorporated in concentrations of 0.001 to 50%, preferably 0.05 to 20% and very preferably 0.1 to 5%.

The specified triglycerides have a wide variety of possible uses. They may be used as pharmaceuticals for the treatment or prevention of disease in which abnormalities of EFAs have been identified. They may be added to foods or be added to or used as nutritional supplements for those who require the particular EFAs for the treatment or prevention of disease. They may also be used in foods or pharmaceuticals for veterinary use. They may be used for skin care.

The triglycerides may be formulated in any way appropriate, as well known to those skilled in the art of preparing pharmaceuticals, skin care products or foods. They may be administered orally, enterally, topically, parenterally, (subcutaneously, intramuscularly, intravenously or by any other route), rectally, vaginally or by any other appropriate route.

Synthetic Examples

The following are examples of synthesis of the triglycerides.

Fourteen triglycerides have been prepared as examples of the range of triglycerides outlined in Table 4, as summarised in Table 5:

TABLE 5

| Code | Triglyceride | TG number (as in Table 2) |
|------|--------------|----------------------------|
| GGA  | GLA/GLA/AA   | 1  |
| GGO  | GLA/GLA/OA   | 3  |
| GGE  | GLA/GLA/EPA  | 4  |
| GGD  | GLA/GLA/DHA  | 4  |
| GAA  | GLA/AA/AA    | 5  |
| GOO  | GLA/OA/OA    | 7  |
| GEE  | GLA/EPA/EPA  | 8  |
| GED  | GLA/EPA/DHA  | 8  |
| GOA  | GLA/OA/AA    | 10 |
| GAE  | GLA/AA/EPA   | 11 |
| GAD  | GLA/AA/DHA   | 11 |

TABLE 5-continued

| Code | Triglyceride | TG number (as in Table 2) |
|------|--------------|---------------------------|
| GOD | GLA/OA/DHA | 14 |
| AED | AA/EPA/DHA | 20 |
| OED | OA/EPA/DHA | 30 |

There are a large number of synthetic routes to triglycerides reported in the literature but we have been concentrating on two main methods. The first uses glycerol mono-protected with a 4-methoxybenzyl group as the starting point. At a later stage in the synthesis this group is removed using a boron reagent, but while this very efficiently removes the protecting group and minimises acyl group scrambling it also causes cis-trans isomerisation of the fatty acid double bonds. This fact coupled with the expense of the reagent severely limits the applicability of this route. The second main route starts with a base-catalysed epoxide ring opening of a glycidol by a fatty acid to yield a monoacyglycerol. This route does lead to a mixture of positional isomers but nevertheless has good potential for larger scale syntheses. Direct reaction between glycerol and a mixture of fatty acids mediated either by DCC/DMAP or p-toluenesulfonic acid has also been carried out using a mixture of two different fatty acids. Assuming that both fatty acids react at equal rates simple probability theory can be applied to predict the distribution of triglyceride products. For example when equal parts of 2 different fatty acids (A,B) are reacted with glycerol using p-toluenesulfonic acid catalysis. Four classes of triglyceride will be formed:

| AAA | 12.5% |
|-----|-------|
| AAB, ABA, BAA | 37.5% |
| ABB, BAB, BBA | 37.5% |
| BBB | 12.5% |

If the fatty acids are in a ratio of 2 parts A: 1 part B the theoretical preparations are:

| AAA | 29.6% |
|-----|-------|
| AAB, ABA, BAA | 44.4% |
| ABB, BAB, BBA | 22.2% |
| BBB | 3.7% |

In actual measurements it should be noted that due to different extinction coefficients at 210 nm (the monitoring wavelength used for the hplc analysis) the percentages measured by hplc are different to the theoretical values.

The same approach can be used to examine the distribution when 3 different fatty acids are used, when in reaction as above ten classes of triglyceride will be formed:

| AAA | 3.7% |
|-----|------|
| BBB | 3.7% |
| CCC | 3.7% |
| AAB, ABA, BAA | 11.1% |
| AAC, ACA, CAA | 11.1% |
| BBA, BAB, ABB | 11.1% |
| BBC, BCB, CBC | 11.1% |
| CCA, CAC, ACC | 11.1% |
| CCB, CBC, BCC | 11.1% |
| ABC, ACB, BAC, BCA, CAB, CBA | 22.2% |

In the light of the large number of triglyceride products and a maximum yield of 22.2% a directed synthesis is preferred.

The invention is illustrated by the following preparative examples, in which the following abbreviations occur:

DCC=dicyclohexylcarbodiimide

DMAP=4-N,N-dimethylaminopyridine

OA=oleic acid (cis-9-octadecenoic acid)

GLA=γ-linolenic acid (cis,cis,cis-6,9,12-octadecenoic acid)

AA=arachidonic acid (cis,cis,cis,cis-5,8,11,14-eicosatetraenoic acid)

EPA=cis,cis,cis,cis,cis-5,8,11,14,17-eicosapentaenoic acid

DHA=cis,cis,cis,cis,cis,cis,-4,7,10,13,16,19-docosahexaenoic acid

Method A—Used for the Preparation of GGA, GGO,GGE, GGD, GAA, GOO an GEE.

Specific Example 1

Preparation of GLA/GLA/EPA

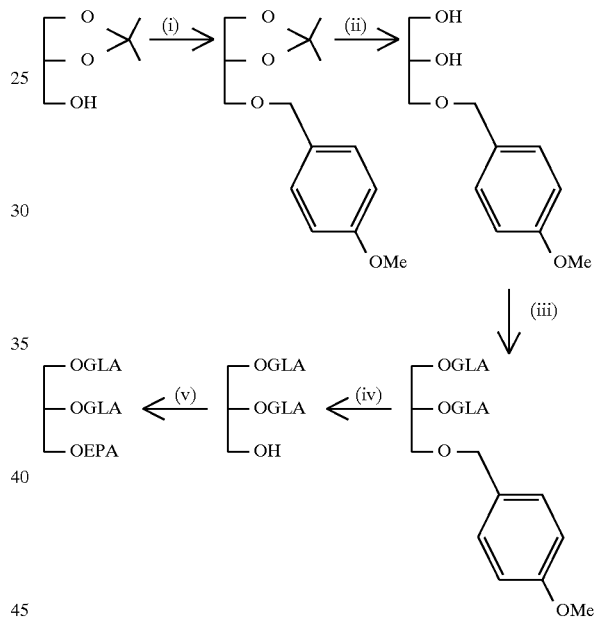

(i) A mixture of solketal (3.3 g, 25 mmol), tetrabutylammonium hydrogen sulfate (425 mg, 1.25 mmol. 5 mol%), sodium hydroxide (6.0 g, 150 mmol), 4-methoxybenzyl chloride (4.7 g, 30 mmol), water (6 ml) and trans-1,2-dichloroethene (20 ml) was stirred vigorously under reflux until tlc (10% acetone/hexane) showed the reaction to be complete (typically 3–7 hours). On completion the reaction mixture was cooled and diluted with water (20 ml) and methylene chloride (20 ml). The organic layer was separated and washed with water until the washings were neutral (4×30 ml). The organic layer was dried (MgSO$_4$) and concentrated to dryness. Purification by flash chromatography (8% acetone/hexane) yielded the fully protected glycerol as a colourless oil.

(ii) A mixturex of the fully protected glycerol (vide supra) (1.0 g), hydrochloric acid (1M, 10 ml) and methanol (15 ml) were stirred together at room temperature for 1 h. (At this point tlc analysis (25% ethyl acetate/hexane) showed complete disapperance of the starting material and the formation of one new spot correspsonding to the product). The bulk of the solvent was removed, brine (20 ml) was added and the product was extracted into methylene chloride (4×30 ml). The combined extracts were dried (MgSO₄) and concentrated to dryness. On standing under high vacuum the product crystallised. On one occasion it was purified by flash chromatography (3% methanol/methylene chloride) although this was not generally necessary. This monoprotected glycerol was the starting point for attachment of the fatty acids.

(iii) A solution of DCC (2.8 g, 13.5 mmol) and DMAP (1.5 g, 12.4 mmol) in methylene chloride (20 ml) was added to a solution of the monoprotected glycerol (1. 15 g, 5.4 mmol) and GLA (95%, 3.5 g, 12.4 mmol) in methylene chloride (40 ml) at room temperature under nitrogen. As the reaction proceeded a precipitate of dicyclohexylurea formed. After 2 h tlc analysis (25% ethyl acetate/hexane) indicated that the reaction was complete. Hexane (60 ml) was added to precipitate more dicyclohexylurea and the reaction was filtered and concentrated to dryness. Purification by flash chromatography (25% ethyl acetate/hexane) yielded the monoprotected diacylglycerol as a colourless oil.

(iv) Bromodimethylborane (85 µl, 0.84 mmol) was added by syringe to a solution of the monoprotected diacylglycerol (310 mg, 0.42 mmol) in methylene chloride (10 ml) at −78° C. (external cooling by dry ice/acetone) under nitrogen. After 3 minutes at −780° C. the reaction was quenched by the addition of diethyl ether (100 ml). Tlc analysis (4% acetone/chloroform) indicated that the reaction had gone substantially towards completion. The mixture was washed with water (5×100 ml), brine (100 ml), dried (MgSO₄) and concentrated to dryness. The product was used direcly in the next step without any further purification.

(v) A solution of DCC (120 mg, 0.55 mmol) and DMAP (60 mg, 0.48 mmol) in methylene chloride (5 ml) Iwas added to a solution of the crude diacylglycerol (0.42 mmol) and EPA (98%, 145 mg, 0.48 mmol) in methylene chloride (10 ml) at room temperature under nitrogen. As the reaction proceeded a precipitate of dicyclohexylurea formed. After 2 h tlc analysis (8% ethyl acetate/hexane) indicated that the reaction was complete. Hexane (30 ml) was added to precipitate more dicyclohexylurea and the reaction was filtered and concentrated to dryness. Purification by flash chromatography (5% ethyl acetate/hexane) yielded the pure triglyceride as a colourless oil.

Method B—Used for the Preparation of GOA and GOD

Specific Example 2

Preparation of GLA/OA/AA (i) as for Method A (ii) as for Method A (iii) A solution of DCC(535 mg, 2.7 mmol) and DMAP (335 mg, 2.7 mmol) in methylene chloride (10 ml) was added dropwise to a cooled (0° C.) solution of the monoprotected glycerol (500 mg, 2.4 mmol) and GLA (95%, 620 mg, 2.2 mmol) in methylene chloride (40 ml) and the resulting solution was stirred at 0° C. for 4 h. During the course of the reaction a fine precipitate of dicyclohexylurea formed. After 4 h tlc analysis (25% ethyl acetate/hexane) indicated complete disappearance of GLA and the formation of 2 new spots corresponding to both positional isomers of monacylated monoprotected glycerol.

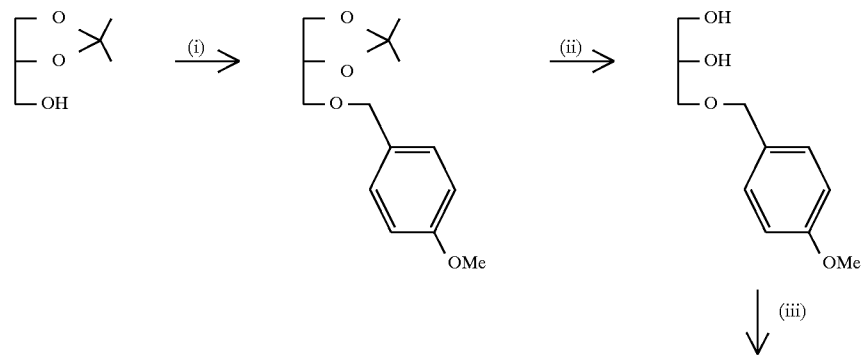

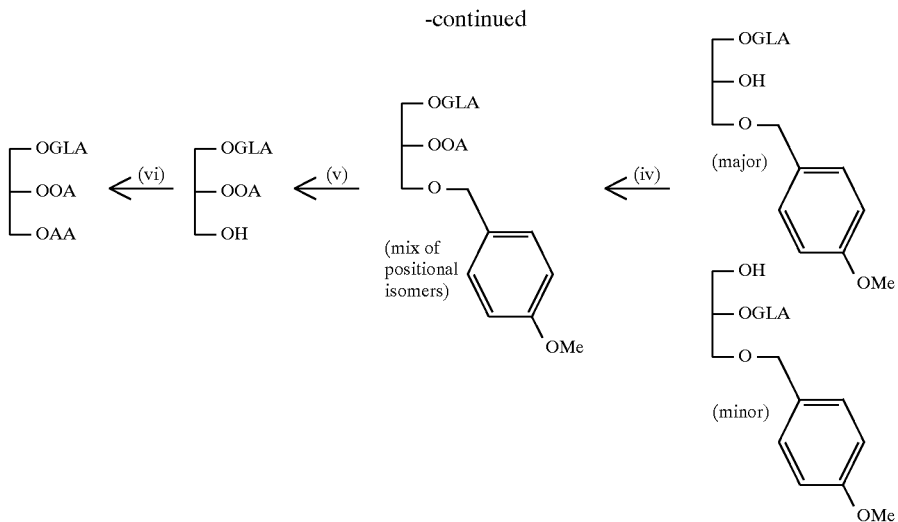

Hexane (50 ml) was added to precipitate more dicyclohexylurea and the mixture was filtered, concentrated to dryness and purified by flash chromatography (25% ethyl acetate/hexane) yielding the product as a colourless oil.

(iv) A solution of DCC (230 mg, 1.11 mmol) and DMAP (115 mg, 0.93 mmol) in methylene chloride (5 ml) was added to a solution of the mixture of monoacylglycerol isomers (400 mg, 0.85 mmol) and OA (99%, 270mg,) 0.93 mmol) in methylene chloride (10 ml) at room temperature under nitrogen. As the reaction proceeded a precipitate of dicyclohexylurea formed. After 3½ h tlc analysis (25% ethyl acetate/hexane) showed the reaction to be complete. Hexane (30 ml) was added to precipitate more dicyclohexylurea and the resulting mixture was filtered, concentrated to dryness and purified by flash chromatography (8% ethyl acetate/hexane) to yield the product as a colourless oil.

(v) Bromodimethylborane (85 μl, 0.84 mmol) was added by syringe to a solution of the monoprotected diacylglycerol (300 mg, 0.41 mmol) in methylene chloride (10 ml) at −78° C. (external cooling by dry ice/acetone) under nitrogen. After 3 minutes at −780° C. the reaction was quenched by the addition of diethyl ether (100 ml). Tlc analysis (4% acetone/chloroform) indicated that the reaction had gone substantially towards completion. The mixture was washed with water (5×10 ml), brine (100 ml), dried (MgSO$_4$) and concentrated to dryness. The product was used directly in the next step without any further purification.

(vi) A solution of DCC (280 mg, 1.37 mmol) and DMAP (150 mg, 1.21 mmol) in methylene chloride (5 ml) was added to a solution of the crude diacylglycerol (1.05 mmol) and AA (95%, 370 mg, 1.21 mmol) in methylene chloride (15 ml) at room temperature under nitrogen. As the reaction proceeded a precipitate of dicyclohexylurea formed. After 2 h tlc analysis (8 % ethyl acetate/hexane) indicated that the reaction was complete. Hexane (30 ml) was added to precipitate more dicyclohexylurea and the reaction was filtered and concentrated to dryness. Purification by flash chromatography (5% ethyl acetate/hexane) yielded the pure triglyceride as a colourless oil.

Method C—Preparation of GED, GAE, GAD, AED and OED

Specific Example 3

Preparation of GED

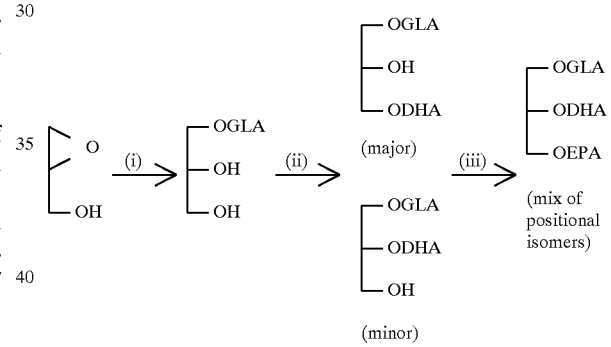

(i) A mixture of GLA (97%, 1.0 g, 3.6 mmol), glycidol (280 mg, 3.73 mmol) and tri-n-butylamine (20 μl. 0.08 mmol) was heated at 85° C. under nitrogen for 5 h. The reaction was then cooled an purified by flash chromatography (5% methanol/methylene chloride) to yield the monoacylglycerol as a colourless oil.

(ii) A solution of DCC (270 mg, 1.31 mmol) and DMAP (160 mg, 1.31 mmol) in methylene chloride (5 ml) was added to a solution of the monoacylglycerol (400 mg, 1.14 mmol) and DHA (98%, 350 mg, 1.08 mmol) in methylene chloride (15 ml) at 0° C. under nitrogen. Tlc analysis (3% methanol/methylene chloride) after 5 h showed the reaction to be complete. Hexane (30 ml) was added to precipitate dicyclohexlyurea and the mixture was filtered, concentrated to dryness and purified by flash chromatography (2% methanol/methiene chloride) to yield a mixture of diacylglycerol positional isomers as a colourless oil.

(iii) A solution of DCC (80 mg, 0.39 mmol) and DMAP (40 mg, 0.35 mmol) in methylene chloride (5 ml) was added to a solution of the diacylglycerol (200 mg, 0.3 mmol) and EPA (98%. 110 mg, 0.35 mmol) in methylene chloride (10 ml) at room temperature under nitrogen. As the reaction proceeded a precipitate of dicyclohexylurea formed. After 2 h tlc analysis (8% ethyl acetate/hexane) indicated that the reaction was complete. Hexane (30 ml) was added to precipitate more dicyclohexylurea and the reaction was filtered and concentrated to dryness. Purification by flash chromatography (5% ethyl acetate/hexane) yielded the pure triglyceride as a colourless oil.

Method D

Specific Example by, Preparation of GGO and GOO as a Mixture (Using a 2:1 Ratio of GLA:OA).

A solution of DCC (725 mg, 3.5 mmol) and DMAP (430 mg, 3.5 mmol) in methylene chloride (10 ml) was added to a solution of glycerol (200 mg, 2.2 mmol), GLA (95%, 610 mg, 2.2 mmol) and OA (99%, 310 mg, 1.1 mmol) in methylene chloride (40 ml) at room temperature under nitrogen. As the reaction proceeded a precipitate dicyclohexylurea formed. After 5 h hexane (50 ml) was added to precipitate more dicyclohexylurea and the reaction was filtered and concentrated to dryness. Purification by flash chromatography (5% ethyl acetate/hexane) yielded the pure triglycerides as a colourless oil.

Method E

Specific Exmaple 5

Preparation of GGO and GOO as a Mixture Using a 1:2 Ratio of GLA:OA).

A solution of DCC (725 mg, 3.5 mmol) and DMAP (430 mg, 3.5 mmol) in methylene chloride (10 ml) was added to a solution of glycerol (200 mg, 2.2 mmol), GLA (98%, 305 mg, 1.1 mmol) and OA (99%, 620 mg, 2.2 mmol) in methylene chloride (40 ml) at room temperature under nitrogen. As the reaction proceeded a precipitate dicyclohexylurea formed. After 5 h hexane (50 ml) was added to precipitate more dicyclohexylurea and the reaction was filtered and concentrated to dryness. Purification by flash chromatography (5% ethyl acetate/hexane) yielded the pure triglycerides as a colourless oil.

Method F

Specific Example 6

Preparation of GGO and GOO as a Mixture (Using a 2:1 Ratio of GLA:OA).

A mixture of glycerol (200 mg, 2.2 mmol), GLA (98%, 610 mg, 2.2 mmol), OA (99%, 305 mmol, 1.1 mmol) and p-toluenesulfonic acid (20 mg) were heated at 140° C. for 5 h under a stream of nitrogen. The reaction was cooled and purified by flash chromatography (5% ethyl acetate/hexane) to yield the pure triglycerides as a colourless oil.

Method G

Specific Example 7

Preparation of GGO and GOO as a Mixture (Using a 1:2 Ratio of GLA:OA).

A mixture of glycerol (200 mg, 2.2 mmol), GLA (98%, 305 mg, 1.1 mmol), OA (99%, 620 mmol, 2.2 mmol) and p-toluenesulfonic acid (20 mg) were heated at 140° C. for 5 h under a stream of nitrogen. The reaction was cooled and purified by flash chromatography (5% ethyl acetate/hexane) to yield the pure triglycerides as a colourless oil.

The products of the above examples have been subject to hplc triglyceride analysis (Table 6) and gc fatty acid analysis (Table 7), by standard methods.

In gc analysis the preparation of the methyl ester derivatives of fatty acids is well known. Boron trifluoride in methanol (12–14% w/v) was used as catalyst. 100 mg of each of the triglycerides was transesterfied and analysed in a Hewlett Packard 5890 Series II equipped with a Supelcowax® 10 capillary column (30 m×0.53 mm×1.0 μm). Injector temperature set at 220° C. and detector temperature at 250° C., the oven temperature was programmed starting at 180° C. for 5 min after which is increased at a rate of 2° C./min until 210° C. was reached and maintained at this temperature for a further 15 mins. 1 μl of each of the methyl esters of the fatty acids was injected using an autosampler, 7673 from Hewlett Packard. Each of the methyl esters of the fatty acids were identified by injecting standards.

TABLE 6

| Example | Triglyceride | Retention Time | Area % (peaks over 2.5%) |
|---|---|---|---|
| 1 | GGA | 11.21 | 83.632 |
|  |  | 13.73 | 10.320 |
|  | GGO | 17.32 | 82.987 |
|  |  | 21.76 | 11.013 |
|  | GGE | 9.00 | 84.844 |
|  |  | 10.69 | 3.452 |
|  |  | 10.89 | 5.031 |
|  | GGD | 9.29 | 86.471 |
|  |  | 11.22 | 9.976 |
|  | GAA | 11.15 | 91.523 |
|  |  | 13.62 | 5.097 |
|  | GOO | 3.28 | 4.434 |
|  |  | 26.87 | 89.002 |
|  | GEE | 7.59 | 89.576 |
|  |  | 9.08 | 2.982 |
| 2 | GOA | 16.31 | 9.243 |
|  |  | 17.77 | 82.816 |
|  |  | 22.31 | 3.018 |
|  | GOD | 15.35 | 91.699 |
|  |  | 19.16 | 4.812 |
| 3 | GED | 6.798 | 90.502 |
|  |  | 8.030 | 6.201 |
|  | GAE | 7.977 | 91.212 |
|  | GAD | 8.198 | 92.140 |
|  |  | 9.802 | 4.202 |
|  | AED | 6.949 | 92.234 |
|  | OED | 10.132 | 98.334 |
| 4 | GGO/GOO | 10.67 | 31.838 (GGG) |
|  |  | 13.09 | 9.143 |
|  |  | 17.30 | 44.518 (GGO) |
|  |  | 21.75 | 3.660 |
|  |  | 29.49 | 6.952 (GOO) |
| 5 | GGO/GOO | 8.711 | 9.270 (GGG) |
|  |  | 13.423 | 33.716 (GGO) |
|  |  | 21.423 | 35.741 (GOO) |
|  |  | 21.942 | 11.338 |
|  |  | 35.684 | 4.651 |
| 6 | GGO/GOO | 8.947 | 35.266 (GGG) |
|  |  | 13.996 | 42.886 (GGO) |
|  |  | 22.974 | 13.228 (GOO) |
| 7 | GGO/GOO | 8.915 | 27.091 (GGG) |
|  |  | 13.943 | 38.959 (GGO) |
|  |  | 22.730 | 22.455 (GOO) |

TABLE 7

| Example | Triglyceride | Retention Time | Area % (peaks over 2.5%) |
|---|---|---|---|
| 1 | GGA | 7.879 | 4.1081 (LA) |
|  |  | 8.568 | 58.6674 (GLA) |
|  |  | 14.140 | 35.2856 (AA) |

TABLE 7-continued

| Example | Triglyceride | Retention Time | Area % (peaks over 2.5%) |
|---|---|---|---|
| | GGO | 6.954 | 33.7482 (OA) |
| | | 7.896 | 3.8946 (LA) |
| | | 8.629 | 60.6707 (GLA) |
| | GGE | 8.589 | 61.1291 (GLA) |
| | | 9.108 | 3.5780 |
| | | 16.017 | 33.0809 (EPA) |
| | GGD | 7.830 | 3.4747 (LA) |
| | | 8.576 | 55.9686 (GLA) |
| | | 9.047 | 3.1251 |
| | | 23.250 | 34.7093 (DHA) |
| | GAA | 8.577 | 30.6452 (GLA) |
| | | 14.168 | 65.1502 (AA) |
| | GOO | 6.969 | 65.1579 (OA) |
| | | 8.570 | 31.6086 (GLA) |
| | GEE | 8.583 | 31.4162 (GLA) |
| | | 16.072 | 63.7405 (EPA) |
| 2 | GOA | 6.936 | 30.8227 (OA) |
| | | 8.576 | 27.4197 (GLA) |
| | | 14.159 | 36.1341 (AA) |
| | GOD | 6.949 | 31.9633 (OA) |
| | | 8.602 | 29.8198 (GLA) |
| | | 23.343 | 34.8294 (DHA) |
| 3 | GED | 8.599 | 29.2576 (GLA) |
| | | 16.056 | 32.4455 (EPA) |
| | | 23.353 | 35.4802 (DHA) |
| | GAE | 8.591 | 31.3688 (GLA) |
| | | 14.173 | 32.2683 (AA) |
| | | 16.043 | 32.9175 (EPA) |
| | GAD | 8.600 | 29.8217 (GLA) |
| | | 14.187 | 31.2864 (AA) |
| | | 23.350 | 35.0575 (DHA) |
| | AED | 14.176 | 30.3248 (AA) |
| | | 16.048 | 31.5008 (EPA) |
| | | 23.333 | 35.1120 (DHA) |
| | OED | 6.956 | 31.4497 (OA) |
| | | 16.063 | 32.3986 (EPA) |
| | | 23.354 | 35.1133 (DHA) |

Use Examples

The following are examples of modes of use of the triglycerides.

1. Any one or any mixture of the triglycerides specified in Table 2 made up in soft or hard gelatin capsules of any size between 100 mg and 1 g and administered to provide a daily dose of between 100 mg and 10 g.

2. Any one or any mixture of the specified triglycerides microencapsulated in gelatin or agar or any other appropriate material, or incorporated into any appropriate material to form a powder which can be taken orally, added to foods, tabletted, encapsulated, packed in sachets or any other appropriate form.

3. Any one or more of the specified triglycerides made up in a whip, liquid, cream or other appropriate form for oral administration.

4. Any one or more of the specified triglycerides made into a cream, ointment or other topical preparation at a concentration ranging from 0.1 to 30%.

5. Any one or more of the specified triglycerides made up into an emulsion suitable for parenteral administration.

6. Any one or more of the specified triglycerides added to any appropriate food material such as a spread, drink, candy, cereal, infant food or bakery product.

We claim:

1. A nutritional supplement or food composition comprising, together with a carrier or diluent, triglycerides, as groups of isomers or singly, containing:
   (a) two residues of an acid, occupying the 1- and 2-positions of the glycerol moiety and selected from oleic acid and the following groups of the acids:
      (i) gamma-linolenic acid (GLA) and dihomo-gamma-linolenic acid (DGLA),
      (ii) arachidonic acid (AA), adrenic acid, and delta-4,7,10, 13, 16-docosapentaenoic acid (the 22:5 n-6 acid),
      (iii) stearidonic acid (SA) and delta-8, 11, 14, 17-eicosatetraenoic acid (the 20:4 n-3 acid),
      (iv) delta-7, 10, 13, 16, 19-docosapentaenoic acid (the 22:5 n-3 acid), and docosahexaenoic acid (DHA),
      and one residue of an acid selected differently therefrom; or
   (b) one residue of an acid selected from the group consisting of oleic acid and the acids of groups (i) to (iv), one residue of an acid selected differently therefrom; and one residue of an acid selected differently again therefrom; with the proviso that where an acid has been selected from one group a subsequent selection is not from that same group.

2. The composition according to claim, 1 wherein said triglycerides constitute more than 10 molar percent of the triglycerides present in the composition.

3. The composition according to claim 2 wherein said triglycerides constitute more than 30 molar percent of the triglycerides present in the composition.

4. The composition according to claim 3 wherein said triglycerides constitute more than 70 molar percent of the triglycerides present in the composition.

5. The composition according to claim 4 wherein said triglycerides constitute more than 90 molar percent of the triglycerides present in the composition.

6. The composition according to claim 1 wherein the composition comprises 0.001 to 50% by weight of said triglycerides.

7. The composition according to claim 1 wherein the composition comprises 0.05 to 20% by weight of said triglycerides.

8. The composition according to claim 1 wherein the composition comprises 0.1 to 5% by weight of said triglycerides.

9. A nutritional supplement or food composition comprising, together with a carrier or diluent, triglycerides, as groups of isomers or singly, containing:
   (a) two residues of an acid, occupying the 1- and 3-positions of the glycerol moiety and selected from oleic acid and the following groups of the acids:
      (i) gamma-linolenic acid (GLA) and dihomo-gamma-linolenic acid (DGLA),
      (ii) arachidonic acid (AA), adrenic acid, and delta-4,7,10, 13, 16-docosapentaenoic acid (the 22:5 n-6 acid),
      (iii) stearidonic acid (SA) and delta-8, 11, 14, 17-eicosatetraenoic acid (the 20:4 n-3 acid),
      (iv) delta-7, 10, 13, 16, 19-docosapentaenoic acid (the 22:5 n-3 acid), and docosahexaenoic acid (DHA),
      and one residue of an acid selected differently therefrom with the proviso that GLA is not selected in the same triglyceride as EPA or DHA, or;
   (b) one residue of an acid selected from the group consisting of oleic acid and the acids of groups (i) to (iv), one residue of an acid selected differently therefrom; and one residue of an acid selected differently again therefrom; with the proviso that where an acid has been selected from one group a subsequent selection is not from that same group.

* * * * *